(12) United States Patent
Jugl et al.

(10) Patent No.: US 9,925,339 B2
(45) Date of Patent: Mar. 27, 2018

(54) COUNTER SYSTEM FOR USE IN A DRUG DELIVERY DEVICE

(71) Applicant: SANOFI-AVENTIS DEUTSCHLAND GMBH, Frankfurt am Main (DE)

(72) Inventors: Michael Jugl, Frankfurt am Main (DE); Axel Teucher, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 461 days.

(21) Appl. No.: 14/435,794

(22) PCT Filed: Oct. 21, 2013

(86) PCT No.: PCT/EP2013/071912
§ 371 (c)(1),
(2) Date: Apr. 15, 2015

(87) PCT Pub. No.: WO2014/064023
PCT Pub. Date: May 1, 2014

(65) Prior Publication Data
US 2015/0290395 A1    Oct. 15, 2015

(30) Foreign Application Priority Data

Oct. 23, 2012 (EP) .................................... 12189589

(51) Int. Cl.
*A61M 5/315* (2006.01)
*A61M 5/31* (2006.01)

(52) U.S. Cl.
CPC ...... *A61M 5/31526* (2013.01); *A61M 5/3156* (2013.01); *A61M 5/31555* (2013.01);
(Continued)

(58) Field of Classification Search
CPC .......... A61M 5/31526; A61M 5/31555; A61M 5/3156; A61M 2005/3126; A61M 2202/0007
(Continued)

(56) References Cited

U.S. PATENT DOCUMENTS 533,575 A    2/1895    Wilkens
5,226,895 A    7/1993    Harris
(Continued)

FOREIGN PATENT DOCUMENTS

EP    0937471    8/1999
EP    0937476    8/1999
(Continued)

OTHER PUBLICATIONS

European Search Report for EP App. No. 12189589, dated May 8, 2013.
(Continued)

*Primary Examiner* — Manuel Mendez
(74) *Attorney, Agent, or Firm* — McDonnell Boehnen Hulbert & Berghoff LLP

(57) ABSTRACT

A counter system for use in a drug delivery device is provided. The counter system comprises a counter element which is a foil, the counter element comprising indentations and indicia associated with the indentations, and a drive member provided with a catch for driving the counter element, wherein the catch engages a first indentation, and wherein, the catch is configured such that, when the drive member moves in a first direction, the counter element does not move and the catch disengages the first indentation and engages a second indentation which is arranged adjacent to the first indentation, and when the drive member moves in a second direction which is opposite to the first direction, the counter element also moves in the second direction.

15 Claims, 4 Drawing Sheets

(52) U.S. Cl.
CPC ............... *A61M 2005/3126* (2013.01); *A61M 2202/0007* (2013.01)

(58) Field of Classification Search
USPC ....... 604/207, 151, 131, 65–67; 128/DIG. 1, 128/DIG. 12, DIG. 13
See application file for complete search history.

(56) References Cited

U.S. PATENT DOCUMENTS

| | | | |
|---|---|---|---|
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,899,698 | B2 | 5/2005 | Sams |
| 6,936,032 | B1 | 8/2005 | Bush, Jr. et al. |
| 7,241,278 | B2 | 7/2007 | Moller |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2006/0153693 | A1 | 7/2006 | Fiechter et al. |
| 2009/0275916 | A1 | 11/2009 | Harms et al. |

FOREIGN PATENT DOCUMENTS

| | | |
|---|---|---|
| EP | 1923083 | 5/2008 |
| WO | 94/06494 | 3/1994 |
| WO | 99/38554 | 8/1999 |
| WO | 01/10484 | 2/2001 |
| WO | 2008/058665 | 5/2008 |
| WO | 2011/039217 | 4/2011 |

OTHER PUBLICATIONS

International Search Report and Written Opinion for Int. App. No. PCT/EP2013/071912, dated Mar. 18, 2014.

COUNTER SYSTEM FOR USE IN A DRUG DELIVERY DEVICE

CROSS REFERENCE TO RELATED APPLICATIONS

The present application is a U.S. National Phase Application pursuant to 35 U.S.C. § 371 of International Application No. PCT/EP2013/071912 filed Oct. 21, 2013, which claims priority to European Patent Application No. 12189589.0 filed Oct. 23, 2012. The entire disclosure contents of these applications are herewith incorporated by reference into the present application.

TECHNICAL FIELD

The present disclosure relates to a counter system for use in a drug delivery device, e.g. a pen-type device and/or an injector-type device.

BACKGROUND

Such drug delivery devices are known from WO 2008/058665 A1, for example.

SUMMARY

It is an object of the present disclosure to provide a counter system for providing an improved drug delivery device. Particularly, a counter system should be provided which facilitates the counting of doses of drug to be dispensed from a drug delivery device.

This object is achieved by the subject-matter of the independent claim. Advantageous embodiments and refinements are subject-matter of the dependent claims.

One aspect of the present disclosure relates to a counter system for use in a drug delivery device comprising a counter element comprising indentations and indicia associated with the indentations, and a drive member provided with a catch for driving the counter element. Thereby, the catch engages a first indentation. The catch is further configured such that, when the drive member moves in a first direction, the counter element does not move and a catch disengages the first indentation and engages a second indentation which is arranged adjacent to the first indentation, and when the drive member moves in a second direction which is opposite to the first direction, the counter element also moves in the second direction. According to this configuration, the counter element can only be moved in the second direction, when the drive member is also moved in the second direction, while a movement of the counter element in the first direction is prevented. Thereby, the counter element may interact or may be engaged to a housing by any suitable means, for example by a pawl or ratchet interaction.

It is an advantage of the provided counter system that, particularly, small dose volumes which are to be dispensed from drug delivery devices can be counted and/or a user or a patient can inspect the filling status of the drug delivery device. Especially, such drug delivery devices may be provisioned to set up and dispense a large number of fixed doses which are contained in a cartridge. The respective drug delivery device may in addition only comprise a comparable low number of interacting parts which form or contribute to the respective counter system. To this effect, tolerances in the mechanics of the drug delivery devices can expediently be kept small. As a consequence, the drug delivery devices provided with the mentioned counter system are easier to operate and safer.

The term "indicia" may refer to any marking or indication on or of the counter element. The indicia may comprise characters, symbols or letters. Preferably the indicia comprise numbers. The indicia being associated with the indentations shall preferably mean that the number of indicia of the counter element equals or corresponds to the number of indentations of the counter element. Thereby, the indicia may be printed on or indicated otherwise to the counter element.

Another aspect of the present disclosure is a drug delivery device comprising the counter system according to the present disclosure. The drug delivery device further comprises a dose button, a cartridge containing a drug and a piston. Alternatively or additionally, the drug delivery device may comprise further components such that it is suitable for dispensing a dose of drug or a plurality thereof.

In an embodiment, the drug delivery device is a pen-type device. As an advantage thereof, the device can be set up in a compact design such that it can be easily stored by a user.

In an embodiment the drug delivery device is an injector-type device.

In an embodiment, the drug delivery device is a fixed-dose device and/or a device, whereby doses are pre-settable. The drug delivery device is preferably suitable to dispense a multitude of fixed doses, i.e. doses of a predominantly constant volume. Preferably, the drug delivery device is suitable to dispense ten or more doses like, e.g., 14 doses. The drug delivery device may further be disposable.

The drug delivery device further comprises a proximal end and a distal end.

In an embodiment, the drug delivery device comprises a needle or a needle assembly. The needle or the needle assembly may be arranged at the distal end of the drug delivery device. Drug may expediently be dispensed through the needle or the needle assembly. The proximal end may be located remote from the user, when drug of the drug delivery device is dispensed or injected into the user or the patient.

In a preferred embodiment, the first direction corresponds to a proximal direction and the second direction corresponds to a distal direction.

In an embodiment the indentations are arranged sequentially along the counter element. Preferably, the counter element is an elongate component, e.g. a strip, which may be arranged inside the drug delivery device. Thereby, the indentations preferably extend along a longitudinal axis of the counter element.

In an embodiment the indentations are holes. Although, the indentations may also be recesses or cut-outs of the counter element, holes provide the advantage that the counter element can be thin and additionally provide structures which can be engaged securely by the catch such that, when the drive member moves in the second direction with respect to the housing, the counter element also moves in that direction. The counter element may be a foil.

In an embodiment, the counter system further comprises a housing having a proximal end and a distal end.

In an embodiment, the counter system is configured such that, when the drive member moves in the first or the second direction, it moves with respect to the housing.

In an embodiment, the counter element is arranged next to an inner wall of the housing. Such an embodiment is particularly expedient, when a respective indicium has to remain visible through the window. Preferably, the counter element is additionally arranged such that its longitudinal axis coincides with a longitudinal axis of the housing which extends from the proximal to the distal end of the housing.

In an embodiment, the housing comprises a window which is arranged and configured such that a respective indicium is visible through the window. This provides the advantage that a user may view the indicium through the window from the outside of the counter system.

In an embodiment, the catch of the counter system comprises a pawl which protrudes from an outer surface of the drive member. The pawl may be engageable to a respective indentation similar or comparable to an interaction of a pawl and a ratchet or to a hook engaging a recess.

When the drive member moves in the first direction with respect to the housing such a pawl disengages the previous indentation and engages an adjacent indentation just by gliding along the counter element which may be arranged next to the drive member. When the drive member moves in a second direction with respect to the housing, the pawl may be configured such that it carries the counter element in a second direction along with the drive member. Therefore, the pawl may comprise a surface which is aligned obliquely with respect to the longitudinal axis of the housing. Thereby, the pawl may form a protrusion which protrudes from a main body of the drive member. The protrusion may then merge on one side to said main body such that the pawl only engage the counter element or an indentation thereof, when the drive member moves in the second direction. Alternatively or additionally, the catch may comprise a spring which is biased when the drive member is moved in the first direction and the catch disengages a respective indentation. The spring may be biased in a direction orthogonal to the longitudinal axis of the housing. The spring may further be released or partly released again, when the catch engages a subsequent or adjacent indentation during movement in a first direction. The spring biased catch may thereby constitute a snap-feature.

In an embodiment, the distance between two indicia corresponds to the distance by which the drive member moves. This enables the counter element to move in the second direction by the interaction of the catch and the respective indentation and the indicia, in particular, the one visible through the window of the housing to move by the same distance.

In an embodiment, the drive member and the counter element are arranged and configured such that, when a first indicium is visible through the window and the drive member moves in the second direction with respect to the housing, a second indicium which is arranged adjacent to the first one becomes visible through the window. As an advantage thereof, the indicia visible through the window may be swept sequentially, when the drive member moves alternately in the first and the second direction with respect to the housing. Thereby, expediently, only one indicium is visible through the window at a time.

In an embodiment, the dose button of the drug delivery device is engaged to the drive member of the counter system. This engagement expediently facilitates that components of the counter system like, e.g. the counter element can be driven by the dose button of the drug delivery device. Preferably, a movement of the drive member is accompanied by a movement of the dose button.

In an embodiment, the drug delivery device is configured such that a pull and push of the dose button effects a dose set and a dose dispense operation, respectively. Thereby, the pull of the dose button may comprise an axial movement of the dose button in the proximal direction with respect to the housing of the drug delivery device and a push of the dose button may comprise an axial movement of the dose button in the distal direction. Expediently, a user or a patient pushes or pulls the dose button manually.

In an embodiment, the drive member, the cartridge and the piston are arranged and configured such that during the dose dispense operation, the drive member drives the piston distally inside the cartridge by which a dose of drug is dispensed from the drug delivery device.

In a preferred embodiment, the drive member of the counter system is a drive sleeve of the drug delivery device. This drive sleeve may be fixed to the dose button of the drug delivery device. In this way, the drive member of the counter system also represents a functional element in the drug delivery device, as it directly or indirectly drives a dose dispensing mechanism. In conclusion, the drive member preferably drives the counter element and the dose dispensing mechanism in the drug delivery device.

The dose dispense operation of the drug delivery device is accompanied by the movement of the drive member in the proximal direction with respect to the housing, as the dose button is engaged to the drive member. Accordingly, the dose set operation is accompanied by the movement of the drive member in the distal direction.

Preferably, the dose set operation is accompanied by the movement of the drive member in the first direction and the dose dispense operation is accompanied by the movement of the drive member in the second direction.

In a preferred embodiment, the housing of the counter system is the housing of the drug delivery device.

The pull and push movement of the dose button, preferably, extend over the distance between two indentations. As this distance corresponds to the distance between two indicia, an indicium adjacent to the respective one which is visible through the window of the housing becomes visible, when the counter element is moved in the second or alternatively in the first direction with respect to the housing. In this way, a user or a patient is given the opportunity to inspect the number of doses of drug already dispensed by the drug delivery device or the ones still remaining in the drug delivery device. The indicia of the counter element may thereby be arranged such that the number of doses visible through the window is counted upwards or increased as well as counted downwards or decreased, when the counter element moves in the second direction.

In an embodiment, the push and the pull of the dose button correspond to a movement of the drive member in the first and the second direction or vice versa, whereby, when the drive member moves in the second direction with respect to the housing, the drive member drives or carries the counter element, and when the drive member moves in the first direction with respect to the housing, the counter element does not move.

A further aspect of the present disclosure is the use of a drug delivery device according to the present disclosure for dispensing doses of drug, wherein the counter system counts the doses of a drug having been dispensed from the drug delivery device at a time.

The mentioned embodiments enable the doses to be dispensed from the drug delivery device to be reliably counted by the counter system and indicated to the user through the window of the housing.

In an embodiment, the use is intended for dispensing a drug or pharmaceutical formulation comprising an active compound selected from the group consisting of insulin, growth hormone, low molecular weight heparine, their analogues and their derivatives.

In an embodiment, the counter system comprises a counter element which is a foil, the counter element comprising indentations and indicia associated with the indentations, and a drive member provided with a catch for driving the counter element, wherein the catch engages a first indentation, and wherein the catch is configured such that, when the drive member moves in a first direction, the counter element does not move and the catch disengages the first indentation and engages a second indentation which is arranged adjacent to the first indentation, and when the drive member moves in a second direction which is opposite to the first direction, the counter element also moves in the second direction.

Features which are described herein above and below in conjunction with different aspects or embodiments may also apply for other aspects and embodiments.

BRIEF DESCRIPTION OF THE FIGURES

Further features and advantageous of the subject matter of the disclosure will become apparent from the following description of the exemplary embodiment in conjunction with the figures, in which.

DETAILED DESCRIPTION

Figure 1:
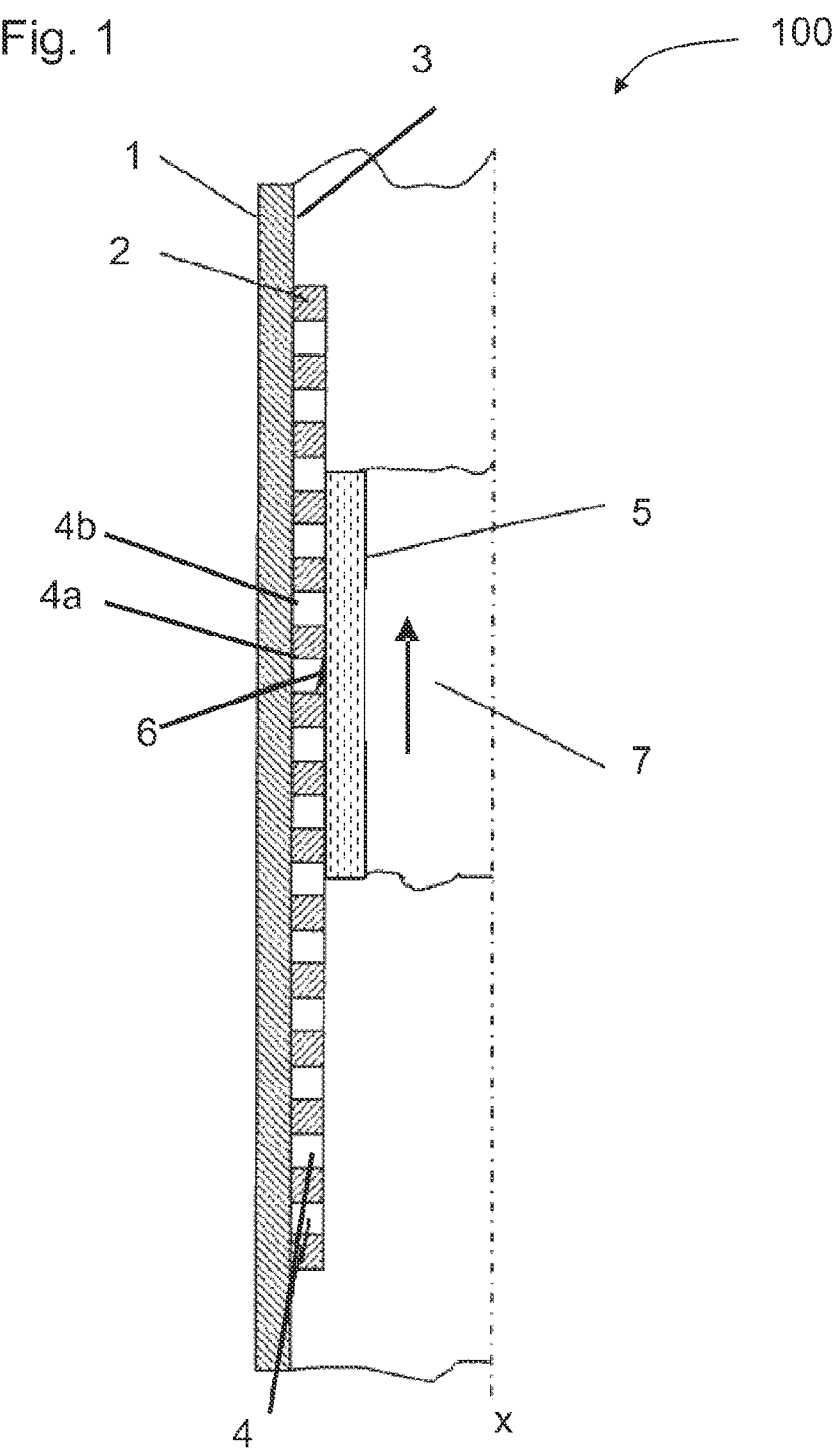
FIG. 1 shows a schematic embodiment of a fraction of the counter system according to the present disclosure in a longitudinal cross-section.

Like elements, elements of the same kind and identically acting elements may be provided with the same reference numerals in the figures. Additionally, the figures may not be true to scale. Rather, certain figures may be depicted in an exaggerated fashion for better illustration of important principles.

FIG. 1 depicts a counter system 100 comprising a housing 1 and a counter element 2. The housing 1 represents only a part of a longitudinal cross-section. The dashed line on the right side may thereby indicate a longitudinal axis of the counter system 100. The counter element 2 is arranged parallel to the housing 1 and next to an inner wall 3 of housing 1. The counter element 2 may be a foil. The thickness of the counter element 2 can, e.g., take values between 0.1 and 0.01 mm. The counter element 2 comprises indentations 4 which are arranged sequentially along the longitudinal axis. The counter system 100 further comprises a drive member 5. The drive member 5 is arranged adjacent to the counter element 2 and comprises a catch 6 which engages an indentation 4a. When the drive member 5 is moved in a proximal direction which is indicated by the arrow 7 with respect to the housing 1, the counter element 2 does not move, and the catch 6 disengages an indentation 4a and engages an indentation 4b which is arranged above indentation 4a. When, subsequently, the drive member 5 is moved in a distal direction with respect to the housing 1 which is opposite to the proximal direction, the counter element 2 is moved along with the drive member 5 in the distal direction, as the catch 6 engages the indentation 4b.

Figure 2:
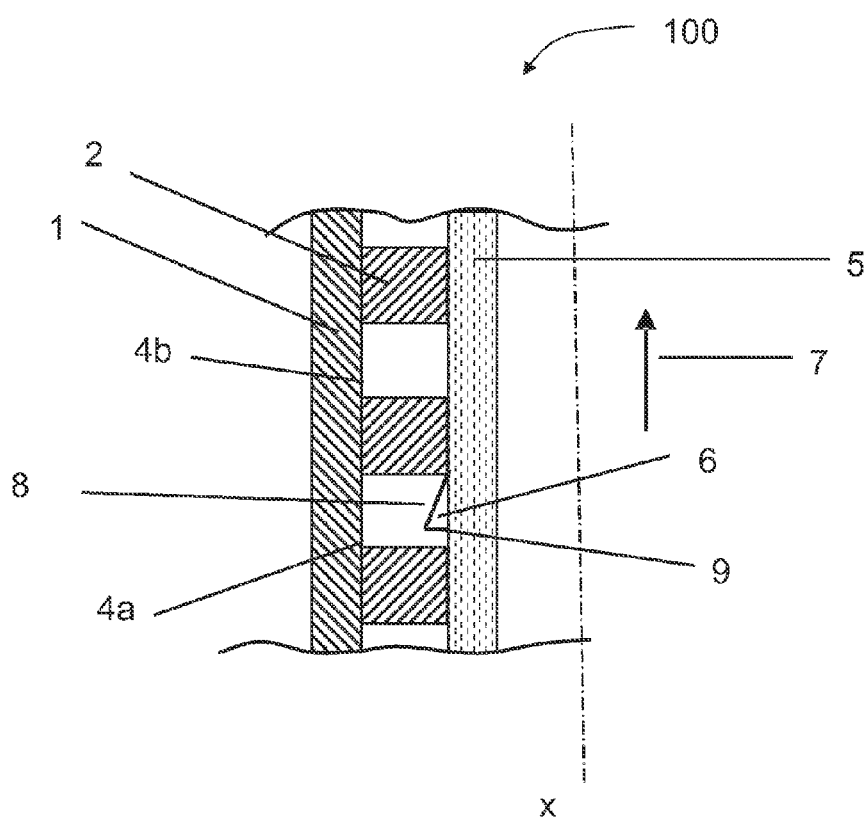
FIG. 2 shows an enlarged portion of the image of FIG. 1.

FIG. 2 shows an enlarged portion of the image from FIG. 1, wherein, e.g., the catch 6 is shown in greater detail. The catch further comprises a surface 8 which is aligned obliquely with respect to the longitudinal axis (see FIG. 1). The surface 8 of the catch 6 enables the drive member 5 to move proximally (see arrow 7) with respect to the housing 1 in such a way that the counter element 2 does not move with respect to the housing 1, as the shape of the catch 6 allows the drive member 5 to glide along the counter element 5. When the catch 6 has engaged indentation 4b and the drive member 5 moves in the distal direction (downwards in FIG. 2), the counter element 2 is then moved along with drive member 5 in the distal direction with respect to the housing 1, as a protrusion 9 of catch 6 engages the counter element 2. The counter element 2 thereby interacts with the housing 1 in such a way that it is distally movable, while a proximal movement with respect to the housing 1 is prevented. Thereby, the counter element 2 may interact or may be engaged to the housing 1 by any suitable means, for example by a pawl or ratchet interaction.

Figure 3:
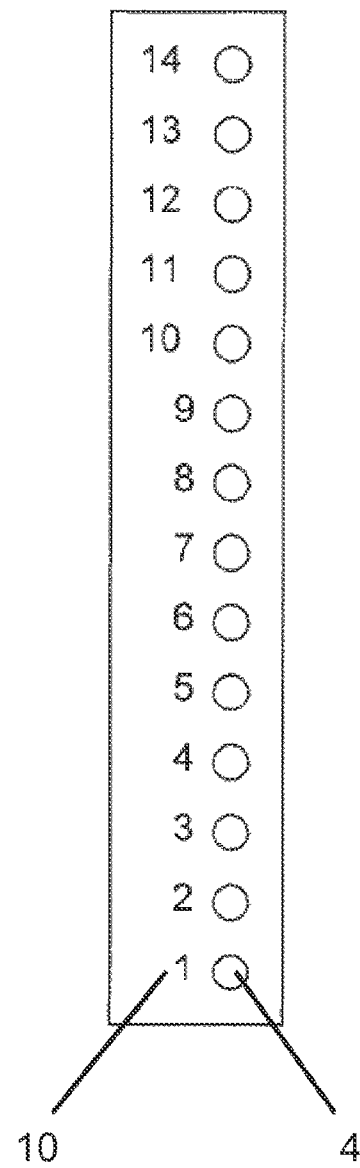
FIG. 3 shows a schematic embodiment of the counter element according to the present disclosure.

FIG. 3 shows a schematic of the counter element 2. The counter element 2 comprises an elongate shape, whereby indentations 4 which are indicated by circles are arranged along a longitudinal axis of the counter element 2 (indicated on the right). The counter element 2 further comprises indicia 10 which are associated with and depicted on the left of the respective indentations 4. The distances between the indentations 4 and the indicia 10 coincide. The indicia are shown as numbers with increasing numeration, as indicated on the left of each indentation 4. The numbers are arranged increasingly from the bottom to the top of the counter element 2. 14 indicia and 14 indentations are indicated. In the illustrated embodiment, a longitudinal axis of the counter element 2 may coincide with the longitudinal axis of the counter system 100.

Figure 4:
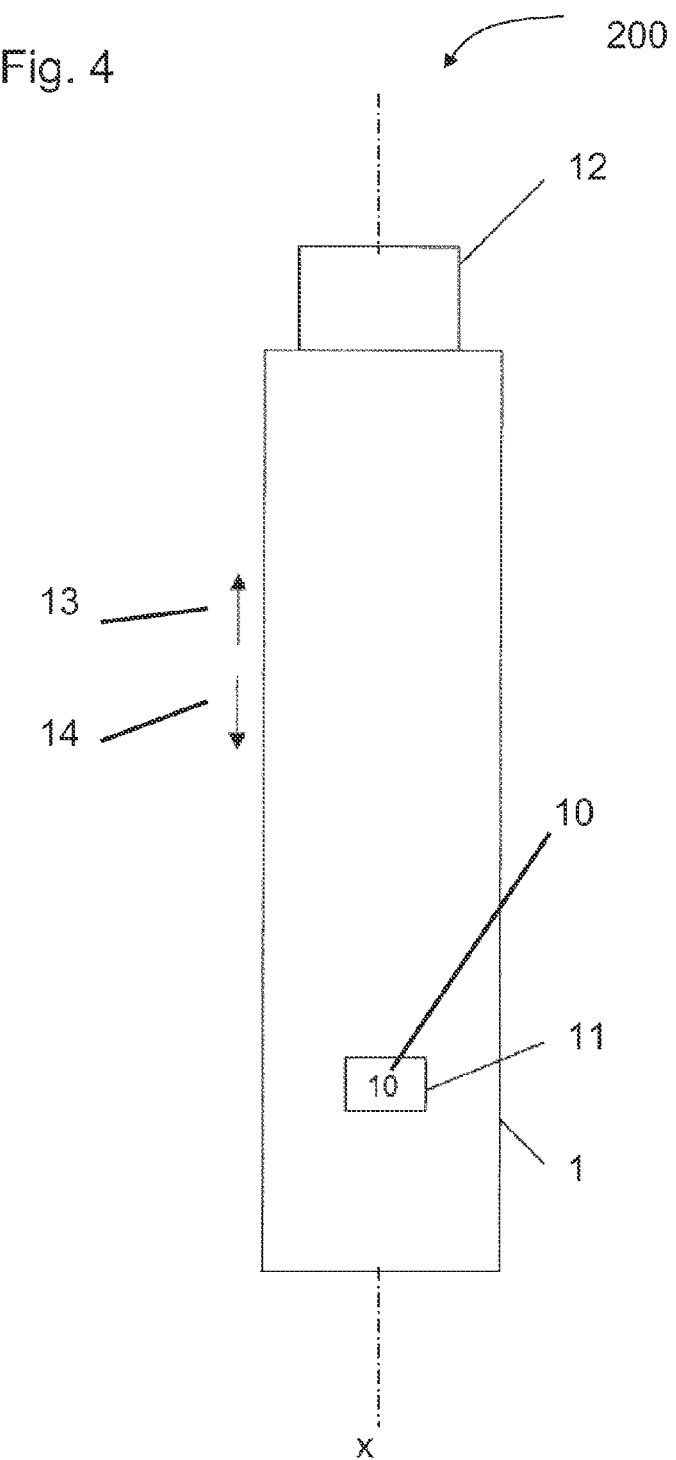
FIG. 4 shows a schematic embodiment of the drug delivery device according to the present disclosure.

FIG. 4 shows a drug delivery device 200 which comprises the counter system 100. The drug delivery device 200 and its function is similar to the one described in WO 2008/058665 A1, the disclosure content of which is hereby incorporated by reference into the description, in particular, as far as the operation of the device is concerned.

The housing 1 of the counter system 100 constitutes the housing of the drug delivery device 200. According to the illustrated embodiment of the counter system 100, the counter element 2 and the drive member 5 of the counter system 100 are arranged inside of housing 1. The drive member 5 of the counter system 100 constitutes a drive sleeve of the drug delivery device 200. Moreover, the longitudinal axis of the counter system 100 coincides with a longitudinal axis of the drug delivery device 200. The drug delivery device 200 further comprises a window 11 which is arranged such that an indicium 10 is visible through the window 11. The drug delivery device 200 further comprises a dose button 12 which is engaged to the drive member 5 of the counter system 100 (see FIGS. 1 and 2) or as the case may be the drive sleeve of the drug delivery device 200.

A pull and push of the dose button 12 with respect to the housing 1 which may be carried out manually by the user effect a dose set and a dose dispense operation of the drug delivery device 200, respectively. As the dose button 12 is engaged to the drive member 5, any movement of the dose button 12 is accompanied by a corresponding movement of the drive sleeve (not shown).

The pull and push movements of the dose button 5 with respect to the housing 1 are carried out in the proximal (see arrow 13) and in the distal direction (see arrow 14), respectively. Said movements expediently extend over a distance corresponding to the distance between two indicia.

In order to be suitable to dispense a dose of drug, the drug delivery device further comprises a cartridge (not shown) containing a drug and a piston (not shown). The dose button 12, the drive member 5, the cartridge and the piston are further configured such that a pull of the dose button 10 effects a proximal movement of the drive member 5 with respect to the housing 1. The proximal direction is indicated by arrow 13. The dose button 12, the drive member 5, the cartridge and the piston are further configured such that a push of the dose button 10 effects a movement in the distal direction with respect to the housing 1. The distal direction is indicated by arrow 14.

The piston or a part thereof may advance inside the cartridge, when the dose button 12 is pushed distally. Alternatively, a further component may be provisioned which is engaged to the piston and which is advanced inside the cartridge, when the dose button 12 is pushed distally. Thereby a dose of drug may be dispensed from the drug delivery device 200. The dispensing can be performed via a needle or a needle assembly (not shown) which may be mounted to a distal end of the drug delivery device 200. The piston or a corresponding component is expediently configured such that it is not moved with respect to the housing, when the dose button 5 is pulled proximally.

According to the illustrated embodiment, a distal movement of the drive member 5 effects a distal movement (14) of the counter element 2 (see FIGS. 1 and 2) with respect to the housing 1. Thereby, the indicium which is visible through the window 11 is increased, as the counter element 2 is moved with respect to the housing 1, and as said movement extends over the distance between two indicia (compare FIG. 3). Along with the distal movement of the drive member 5, also a dose of drug is dispensed from the drug delivery device 200.

The maximum number of doses of drug contained in the cartridge of the drug delivery device 200 may correspond to the number of indicia 10 and optionally to the number of indentations, such that, when a dose of the drug delivery device is dispensed for the first time, the first indicium or the first number becomes visible through the window 11 of the housing 1.

Although in the mentioned embodiment, the claimed first direction corresponds to a proximal direction, and the claimed second direction corresponds to a distal direction, it is also perceivable and included within the present disclosure that the claimed first direction corresponds to a distal direction and the claimed second direction corresponds to a proximal direction. In the latter embodiment, the counter element would be moved along with the drive member, when the dose button is pulled proximally with respect to the housing. Accordingly, the counter element would not move with respect to the housing, when the dose button is pushed distally. Thereby, the catch of the drive member would need to be oriented such that the protrusion of the catch carries the counter element proximally, when the dose button is pulled. This first embodiment, however, provides the advantage that a dose of drug of the drug delivery device is counted instantaneously when this dose is actually dispensed from the drug delivery device.

The term "drug" or "pharmaceutical formulation" as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys) 6-NH2,
H-Asn-(Glu)5-des Pro36, Pro37, Pro38 [Met(O)14, Trp(O2) 25, Asp28] Exendin-4(1-39)-(Lys) 6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

The invention claimed is:

1. A counter system for use in a drug delivery device comprising:
   a counter element which is a foil, the counter element comprising indentations and indicia associated with the indentations, and
   a drive member provided with a catch for driving the counter element, wherein the catch engages a first indentation, and wherein the catch is configured such that, when
   the drive member moves in a first direction, the counter element does not move and the catch disengages the first indentation and engages a second indentation which is arranged adjacent to the first indentation, and when
   the drive member moves in a second direction which is opposite to the first direction, the counter element also moves in the second direction.

2. The counter system according to claim 1, wherein the indentations are arranged sequentially along the counter element.

3. The counter system according to claim 1, wherein the indentations are holes.

4. The counter system according to claim 1, wherein the catch comprises a pawl which protrudes from an outer surface of the drive member.

5. The counter system according to claim 1, further comprising a housing having a proximal end and a distal end, wherein the housing comprises a window which is arranged and configured such that a respective indicium is visible through the window.

6. The counter system according to claim 5, wherein the counter element is arranged next to an inner wall of the housing.

7. The counter system according to claim 5, wherein, when the drive member moves in the first or the second direction, it moves with respect to the housing, and wherein the distance between two indicia corresponds to the distance by which the drive member moves.

8. The counter system according to claim 5, wherein the drive member and the counter element are arranged and configured such that, when a first indicium is visible through the window and the drive member moves in the second direction with respect to the housing, a second indicium which is arranged adjacent to the first one becomes visible through the window.

9. A drug delivery device comprising the counter system as defined in claim 1 further comprising a dose button, a cartridge containing a drug, and a piston.

10. The drug delivery device according to claim 9, wherein the drug delivery device is configured such that a pull and push of the dose button effect a dose set and a dose dispense operation, respectively, and the pull and the push of the dose button correspond to a movement of the drive member in the first and the second direction or vice versa, whereby, when the drive member moves in the second direction with respect to the housing, the drive member drives or carries the counter element, and when the drive member moves in the first direction with respect to the housing, the counter element does not move.

11. The drug delivery device according to claim 9, wherein the dose button is engaged to the drive member, and wherein the drive member, the cartridge and the piston are arranged and configured such that during the dose dispense operation, the drive member drives the piston distally inside the cartridge by which a dose of drug is dispensed from the drug delivery device.

12. The drug delivery device according to claim 9, wherein the drive member is a drive sleeve of the drug delivery device, and the housing is a housing of the drug delivery device.

13. The drug delivery device according to claim 9, which is a pen-type device.

14. Use of a drug delivery device as defined in claim 9 for dispensing doses of drug, wherein the counter system counts said doses of drug to be dispensed from the drug delivery device.

15. Use of a drug delivery device according to claim 14, for dispensing a pharmaceutical formulation comprising an active compound selected from the group consisting of insulin, growth hormone, low molecular weight heparin, their analogues and their derivatives.

* * * * *